United States Patent
Takano et al.

(10) Patent No.: US 6,242,651 B1
(45) Date of Patent: Jun. 5, 2001

(54) PROCESS FOR THE PREPARATION OF N,N'-DIALKYLALKANEDIAMINES

(75) Inventors: Yasuhiro Takano; Kaoru Sakadera, both of Fukuoka; Jyoji Morisaki, Kumamoto; Kunihiro Yamada, Fukuoka; Hideki Mizuta, Fukuoka; Hisato Itoh, Fukuoka, all of (JP)

(73) Assignee: Mitsui Chemicals, Inc. (JP)

( * ) Notice: Subject to any disclaimer, the term of this patent is extended or adjusted under 35 U.S.C. 154(b) by 0 days.

(21) Appl. No.: 09/673,749

(22) PCT Filed: Mar. 15, 2000

(86) PCT No.: PCT/JP00/01576

§ 371 Date: Oct. 20, 2000

§ 102(e) Date: Oct. 20, 2000

(87) PCT Pub. No.: WO00/56697

PCT Pub. Date: Sep. 28, 2000

(30) Foreign Application Priority Data

Mar. 19, 1999 (JP) .................................................. 11-074734

(51) Int. Cl.⁷ ................................................. C07C 209/08
(52) U.S. Cl. ............................................................ 564/482
(58) Field of Search ............................................... 564/482

(56) References Cited

U.S. PATENT DOCUMENTS 4,053,516 * 10/1977 Hammerstrom et al. ............ 564/498

FOREIGN PATENT DOCUMENTS 0254229   1/1988   (EP) .
2013180   8/1979   (GB) .

\* cited by examiner

*Primary Examiner*—Johann Richter
*Assistant Examiner*—Brian J. Davis
(74) *Attorney, Agent, or Firm*—Burns, Doane, Swecker & Mathis, L.L.P.

(57) ABSTRACT

A preparation process of N,N'-dialkylalkanediamine by reacting dihaloalkane with lower alkylamine characterized by carrying out the reaction with controlling the residual amount in the reaction system of haloalkaneamine intermediate represented by the formula (4):

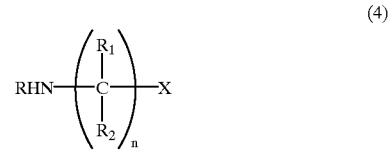

(4)

wherein R is a lower alkyl group, $R_1$ and $R_2$ are a hydrogen atom or a lower alkyl group, X is a chlorine, bromine or iodine atom, and n is an integer of 2 to 6, and the invention inhibits formation of by-products cyclic dialkyldiamine and trialkylalkanetriamine and can provide desired N,N'-dialkylalkanediamine with a high yield.

22 Claims, No Drawings

PROCESS FOR THE PREPARATION OF N,N'-DIALKYLALKANEDIAMINES

TECHNICAL FIELD

This application is a 371 of PCT JP00/01576 filed Mar. 15, 2000.

The present invention relates to a novel preparation process of N,N'-dialkylalkanediamine. More particularly, in the preparation of the N,N'-dialkylalkanediamine by reaction of dihaloalkane with lower alkylamine, the invention relates to a process for preparing desired N,N'-dialkylalkanediamine in a high yield by inhibiting formation of unfavorable by-products such as cyclic dialkyldiamine and trialkylalkanetriamine.

BACKGROUND ART

The preparation process of N,N'-dialkylalkanediamine has been known for a long time, and many processes have been proposed. For example, J. uber die Fortshritteder Chemie, 389(1859) has reported a process for preparing N,N'-diethyl-1,2-ethanediamine by reacting dibromoalkane with alkylamine.

A process for obtaining N,N'-dimethyl-1,2-propanediamine has been described in J. Chem. Soc., 214 (1947).

Further, processes for preparing N,N'-dimethyl-1,3-propanediamine and N,N'-dimethyl-1,2-ethanediamine have also been known.

Japan Laid Open Patent SHO 57-120570 has disclosed a process for preparing 1,3-dimethyl-2-imidazolidinone via N,N'-dimethyl-1,2-ethanediamine as an intermediate by reacting 1,2-dichloroethane, water, liquid methylamine and carbon dioxide in an autoclave.

Further, a reaction of dichloroalkane with primary lower alkylamine has been found as a process for preparing N,N'-dialkylalkanediamine. Various investigations have been carried out on the reaction. For example, a process for carrying out the reaction in the presence of a nickel compound and/or copper compound and a process for carrying out the reaction substantially in the absence of moisture have been proposed in Japan Laid Open Patent SHO 62-129256.

These processes for preparing N,N'-dialkylalkanediamine by reaction of dihaloalkane and alkylamine can provide the desired product in a high yield and thus are favorable processes.

The processes can provide N,N'-dialkylalkanediamine in a yield of 80 to 85%. However, 1 to 5% of cyclic dialkyldiamine and 9 to 13% of trialkylalkanetriamine are formed as impurities at the same time. The whole amount of impurities including other by-products is considerably large. As a result, enhancement of equipment has been required for the purification of thus obtained N,N'-dialkylalkanediamine.

Consequently, as to the preparation of N,N'-dialkylalkanediamine, it has been desired to develop a process which can inhibit formation of cyclic dialkyldiamine, trialkylalkanetriamine and other impurities and can provide high purity N,N'dialkylalkanediamine in a high yield. It has also been demanded that N,N'-alkylalkanediamine is produced by such a process in order to simplify the purification operation.

DISCLOSURE OF INVENTION

One object of the invention is to solve the above problems on the known preparation process of N,N'-dialkylalkanediamine and to increase the yield of N,N'-dialkylalkanediamine.

Another object of the invention is to provide a novel preparation process of N,N'-dialkylalkanediamine which can inhibit formation of cyclic dialkyldiamine and trialkylalkanetriamine, can give high purity and high yield, and has no requirement to make purification equipment complex and large scale.

The present inventors have carried out an intensive investigation in order to solve the above problems. That is, various investigations have been carried out on the reaction between dihaloalkane and alkylamine. The reaction mechanism was elucidated in the main reaction and a side reaction for forming cyclic dialkyldiamine and trialkylalkanetriamine. On the basis of these investigation results, the present invention, that is, a preparation process of N,N'-dialkylalkanediamine has been completed.

On the basis of the elucidated mechanism on the main reaction for forming the desired product and the side reaction for forming the by-products, the present inventors have found that a haloalkaneamine intermediate generates in the course of forming N,N'-dialkylalkanediamine by reaction of dihaloalkane and alkylamine, and that the object of the invention can be achieved by proceeding the reaction while controlling the residual amount of haloalkaneamine intermediate in the reaction system, that is, concentration in the reaction mixture. Thus the present invention has been completed.

In the process of the invention, the haloalkaneamine intermediate formed by reaction of dihaloalkane and alkylamine is controlled to 0.002 mol or less, preferably 0.001 mol or less per 1 mol of alkylamine in the reaction system. Further, the object of the invention can be achieved by reacting the haloalkaneamine intermediate with alkylamine which serves as a solvent. The embodiment for realizing the process is dropwise addition of dihaloalkane in a batch type reactor or use of vessel type continuous reactor, preferably, multistage vessel type continuous reactor, more preferably tubular continuous reactor.

In the process, alkylamine and dihaloalkane are charged to the reactor, dihaloalkane is preferably added continuously or by portions, the reaction is proceeded with controlling the amount of haloalkaneamine intermediate in the above range, formation of cyclic dialkyldiamine and trialkylalkanetriamine is inhibited, and thus high purity N,N'-dialkylalkanediamine can be obtained in a high yield.

That is, the aspect of the present invention is illustrated below.

(1) A preparation process of N,N'-dialkylalkanediamine by reacting dihaloalkane represented by the formula (1):

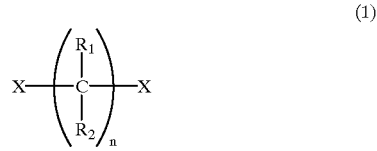

wherein $R_1$ and $R_2$ are a hydrogen atom or a lower alkyl group, X is a chlorine, bromine or iodine atom, and n is an integer of 2 to 6, with lower alkylamine represented by the formula (2):

wherein R is a lower alkyl group, to obtain N,N'-dialkylalkanediamine represented by the formula (3):

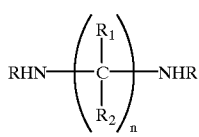

(3)

wherein $R_1$ and $R_2$ are a hydrogen atom or a lower alkyl group, X is a chlorine, bromine or iodine atom, and n is an integer of 2 to 6, characterized in that the reaction is carried out with controlling the residual amount of haloalkaneamine intermediate represented by the formula (4):

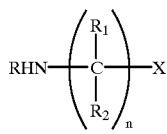

(4)

wherein R is a lower alkyl group, $R_1$ and $R_2$ are a hydrogen atom or lower alkyl group, X is a chlorine, bromine or iodine atom, and n is an integer of 2 to 6, to 0.002 mol or less for 1 mol of lower alkylamine represented by the formula (2).

(2) A preparation process according to item (1) wherein the lower alkylamine represented by the formula (2) is used in amount of 5 mols or more for 1 mol of dihaloalkane represented by the formula (1).

(3) A preparation process according to item (1) wherein the reaction of dihaloalkane with lower alkylamine is carried out by dropwise addition of dihaloalkane to lower alkylamine in a batch reactor.

(4) A preparation process according to item (1) wherein the reaction of dihaloalkane with lower alkylamine is carried out in a vessel type continuous reactor or a tubular continuous reactor.

(5) A preparation process according to item (1) wherein the reaction of dihaloalkane with lower alkylamine is carried out in a multistage vessel type continuous reactor.

(6) A preparation process according to item (1) wherein the reaction of dihaloalkane with lower alkylamine is carried out in a tubular continuous reactor.

(7) A preparation process according to item (6) wherein the reaction is carried out by feeding dihaloalkane represented by the formula (1) and lower alkylamine represented by the formula (2) to a tubular continuous reactor, and dihaloalkane is added by portions or continuously at a position capable of controlling a residual amount in the reactor tube of haloalkaneamine represented by the formula (4), to 0.002 mol or less for 1 mol of lower alkylamine.

(8) A preparation process according to one of items 1 to 7 wherein the residual amount in the reaction system of haloalkaneamine represented by the formula (4) is 0.001 mol or less for 1 mol of lower alkylamine represented by the formula (2).

(9) A preparation process according to one of item 1 to 8 wherein the reaction is carried out at temperature of 50 to 250° C.

The invention can react dihaloalkane and lower alkylamine and inhibit formation of by-product cyclic dialkyldiamine and trialkylalkanetriamine which cause problems in the conventional preparation process, and provide desired N,N'-dialkylalkanediamine in a high yield. The process can provide a large amount of N,N'-dialkylalkanediamine continuously with a high yield within a short time, with less formation of by-product, and thus is an excellent production process in industry.

BEST MODE FOR CARRYING OUT THE INVENTION

According to the analyses of the present inventors, the reaction dihaloalkane with alkylamine and formation of by-products cyclic dialkyldiamine and trialkylalkanetriamine were on the basis of a complex mechanism. Accordingly, the present inventors have carried out an intensive investigation in order to elucidate the mechanism and completed the invention.

In the process of the invention, halogen on dihaloalkane causes dehydrohalogenation reaction with hydrogen on alkylamine. As a result, dihaloalkane is substituted with alkylamine to form N,N'-dialkylalkanediamine.

In the conventional preparation process, the desired product is N,N'-dialkylalkanediamine and additionally, formation of by-product cyclic dialkyldiamine and trialkylalkanetriamine is inevitable. These facts illustrate complex reaction mechanism and extreme difficulty for elucidating the reaction mechanism and investigating the reaction conditions in order to achieve the object of the invention.

In the course of forming N,N'-dialkylalkanediamine from dihaloalkane and alkylamine, the main reactions are formation of a haloalkaneamine intermediate by reacting dihaloalkane with alkylamine and formation of N,N'-dialkylalkanediamine by reacting the resultant haloalkaneamine with alkylamine. Additionally, side reactions which occur in parallel with these main reactions are formation of cyclic dialkyldiamine by reaction of the intermediate haloalkaneamine with each other and formation of trialkylalkanetriamine by reaction of the haloalkaneamine intermediate and the desired product N,N'-dialkylalkanediamine.

In these reactions, reactivity of the haloalkaneamine intermediate with alkylamine, haloalkaneamine and N,N'-dialkylalkanediamine, respectively, was found to have close relationship with the main reaction for forming N,N'-dialkylalkanediamine and the side reactions for forming cyclic dialkyldiamine and trialkylalkanetriamine.

As a result of an extensive investigation on these reactions, the present invention has been completed by the process characterized below.

That is, it is important that (1) alkylamine has a high molar ratio to dihaloalkane, and that (2) haloalkaneamine is formed by reaction of dihaloalkane and alkylamine and thus the reaction is carried out with controlling the residual amount of haloalkaneamine intermediate in the reaction system to a prescribed level or less. For example, in the reaction system to be employed, alkylamine itself is used as a solvent and dihaloalkane is added continuously or by portions to alkylamine with controlling the residual amount of haloalkane amine intermediate to a prescribed level or less.

Such a reaction mode cannot be obtained when the raw materials are charged at one time to a batch reactor. The reactors which can be used are a batch reactor having an apparatus for dropwise adding dihaloalkane, vessel type continuous reactor and multistage vessel type continuous reactor.

Dihaloalkane which can be used in the invention is represented by the formula (1):

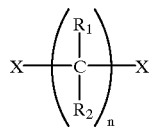

wherein $R_1$ and $R_2$ are a hydrogen atom or lower alkyl group, X is a chlorine, bromine or iodine, and n is an integer of 2 to 6.

Representative dihaloalkane includes, for example, 1,2-dichloroethane, 1,2-dichloropropane, 1,3-dichloropropane, 1,3-dichloro-2,2-dimethylpropane, 1,3-dichloro-2,2-diethylpropane, 1,3-dichlorobutane, 1,4-dichloro-2,2-dimethylbutane, 1,4-dichloro-2,3-dimethylbutane, 1,4-dichloro-2,2-dimethylbutane, 1,4-dichloro-2,2-dipropylbutane, 1,2-dichloropentane, 1,5-dichloropentane, 1,5-dichloro-2,2-diethylpentane, 1,5-dichloro-2,3-dimethylpentane, 1,5-dichloro-2,4-dimethylpentane, 1,2-dichlorohexane, 1,6-dichlorohexane, 1,6-dichloro-2,2-dimethylhexane, 1,6-dichloro-2,2-dipropylhexane, 1,6-dichloro-2,3-diethylhexane, 1,6-dichloro-2,5-diethyl hexane, 1,2-dibromoethane, 1,2-dibromopropane, 1,3-dibromopropane, 1,3-dibromo-2,2-dimethylpropane, 1,3-dibromo-2,2-diethylpropane, 1,3-dibromobutane, 1,4-dibromo-2,2-dimethylbutane, 1,4-dibromo-2,3-dimethylbutane, 1,4-dibromo-2,2-diethylbutane, 1,4-dibromo-2,2-dipropylbutane, 1,2-dichloropentane, 1,5-dibromopentane, 1,5-dibromo-2,2-diethylpentane, 1,5-dibromo-2,3-dimethylpentane, 1,5-dibromo-2,4-dimethylpentane, 1,2-dibromohexane, 1,6-dibromohexane, 1,6-dibromo-2,2-dimethylhexane, 1,6-dibromo-2,2-dipropylhexane, 1,6-dibromo-2,3-diethylhexane, 1,6-dibromo-2,5-diethylhexane, 1,2-diiodoethane, 1,2-diiodopropane, 1,3-diiodopropane, 1,3-diiodo-2,2-dimethylpropane, 1,3-diiodo-2,2-diethylpropane, 1,3-diiodobutane, 1,4-diiodo-2,2-dimethylbutane, 1,4-diiodo-2,3-dimethylbutane, 1,4-diiiodo-2,2-diethylbutane, 1,4-diiodo-2,2-dipropylbutane, 1,2-diiodopentane, 1,5-diiodopentane, 1,5-diiodo-2,2-diethylpentane, 1,5-diiodo-2,3-dimethylpentane, 1,5-diiodo-2,4-dimethylpentane, 1,2-diiodohexane, 1,6-diiodohexane, 1,6-diiodo-2,2-dimethylhexane, 1,6-diiodo-2,2-dipropylhexane, 1,6-diiodo-2,3-diethylhexane and 1,6-diiodo-2,5-diethylhexane.

Lower alkylamine which can be used in the invention is represented by the formula (2):

R—NH$_2$   (2)

wherein R is a lower alkyl group, and includes, for example, methylamine, ethylamine, 1-propylamine, 2-propylamine, n-butylamine, isobutylamine, sec-butylamine and t-butylamine.

Further, N,N'-dialkylalkanediamine which can be obtained by the process of the invention is represented by the formula (3):

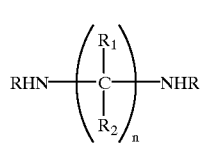

wherein $R_1$ and $R_2$ are a hydrogen atom or lower alkyl group and can be the same or different to each other, R is a lower alkyl group, and n is an integer of 2 to 6.

Exemplary compounds represented by the formula (3) include N,N'-dimethyl-1,2-ethanediamine, N,N'-dimethyl-1,2-propanediamine, N,N'-dimethyl-1,3-propanediamine, N,N',2,2-tetramethyl-1,3-propanediamine, N,N'-dimethyl-2,2-diethyl-1,3-propanediamine, N,N'-dimethyl-1,3-butanediamine, N,N'-dimethyl-1,4-butanediamine, N,N'-dimethyl-2,3-diethyl-1,4-butanediamine, N,N'-dimethyl-2,2-diethyl-1,4-butanediamine, N,N'-dimethyl-2,2-dipropyl-1,4-butanediamine, N,N'-dimethyl-1,2-pentanediamine, N,N'-dimethyl-1,5-pentanediamine, N,N'-dimethyl-2,2-dimethyl-1,5-pentanediamine, N,N'-dimethyl-2,3-dimethyl-1,5-pentanediamine, N,N'-dimethyl-2,4-dimethyl-1,5-pentanediamine, N,N'-dimethyl-1,2-hexanediamine, N,N'-dimethyl-1,6-hexanediamine, N,N'-dimethyl-2,2-dimethyl-1,6-hexanediamine, N,N'-dimethyl-2,2-dipropyl-1,6-hexanediamine, N,N'-dimethyl-2,3-diethyl-1,6-hexanediamine and N,N'-dimethyl-2,5-diethyl-1,6-hexanediamine.

The present invention is a preparation process of N,N'-dialkylalkanediamine represented by the formula (3) by reacting dihaloalkane of the formula (1) with lower alkylamine of the formula (2), wherein the improvement comprises carrying out the reaction with controlling the residual amount in the reaction system of the haloalkaneamine intermediate represented by the formula (4):

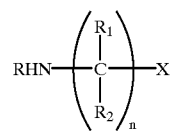

wherein $R_1$ and $R_2$ are a hydrogen atom or lower alkyl group and can be the same or different, R is a lower alkyl group and n is an integer of 2 to 6.

Haloalkaneamine forms by reaction of one of the halogen atoms on dihaloalkane of the formula (1) with lower alkylamine of the formula (2), and is N-alkyl-monohaloalkaneamine which corresponds to various exemplified compounds of dihaloalkane represented by the formula (1) above.

In the process of the invention, the amount of lower alkylamine is generally 5 mols or more, preferably, 10 to 100 mols, more preferably 15 to 100 mols for 1 mol of dihaloalkane.

The reaction of these raw materials leads to formation of haloalkaneamine intermediate, and the important point of the invention is to control the residual amount of haloalkaneamine intermediate to a specific level in the reaction system.

The above amounts of raw material compounds are preferably used in order to control the amount of haloalkaneamine in the reaction system to a range specified in the invention.

The residual amount of haloalkaneamine in the reaction system corresponds to a ratio (content) of haloalkaneamine to lower alkylamine in the reaction mixture. The amount is usually 0.0005 to 0.002 mol, preferably 0.002 mol or less, more preferably 0.001 mol or less for 1 mol of lower alkylamine.

That is, the range of the haloalkaneamine intermediate in the reaction system is specified by the following formulation.

| | |
|---|---|
| Usually | $0.0005 \leq [HA]m/[AM]m \leq 0.002$ |
| Preferably | $[HA]m/[AM]m \leq 0.002$ |
| More preferably | $[HA]m/[AM]m \leq 0.001$ |

In the above formulation, [HA]m indicates the molar number of haloalkaneamine intermediate and [AM]m indicates the molar number of lower alkylamine.

The residual amount of haloalkaneamine exceeding 0.002 mol ratio in the reaction system leads to increase in the formation of unfavorable by-products cyclic dialkyldiamine and trialkylalkanetriamine. The reason of such phenomenon is considered as follows. The reaction velocity for forming N,N'-dialkylalkanediamine from residual haloalkaneamine intermediate in the reaction system and lower alkylamine is unexpectedly lower than the reaction velocity for forming the haloalkaneamine intermediate from dihaloalkane and lower alkylamine. As a result, the haloalkaneamine intermediate is accumulated in the reaction system. Furthermore, the reaction of the haloalkaneamine intermediate with each other or with the desired N,N'-dialkylalkanediamine proceeds in an unexpectedly high velocity and is liable to form by-products.

In the process of the invention, in order to control the residual amount of the haloalkaneamine intermediate in the reaction system to a prescribed level or less and to preferentially carry out formation of N,N'-dialkylalkanediamine, lower alkylamine is used in a great excess to dihaloalkane, dihaloalkane is added preferably by portions or continuously and the desired N,N'-dialkylalkanediamine is prepared by controlling the haloalkaneamine in the reaction system to a prescribed level or less.

The residual amount of haloalkaneamine intermediate can be analyzed by collecting the reaction mixture at a desired portion of the reactor and immediately measuring by, for example, gas chromatography. Lower alkylamine and/or dihaloalkane to be fed to the reaction system can be controlled by adding continuously or by portions through a feeding port which is installed at one or more desired parts on the reactor.

The reaction temperature is usually 50 to 150° C. The temperature range is advantageous for controlling the residual amount of the haloalkaneamine intermediate in the reaction system. The reaction temperature is preferably 80 to 140° C. in order to increase the yield of N,N'-dialkylalkanediamine and inhibit formation of by-products cyclic dialkyldiamine and trialkylalkanetriamine.

No particular limitation is imposed upon the reaction pressure. The reaction pressure is usually 0.2 to 12 MPa, preferably 2 to 8 MPa.

No particular limitation imposed upon the reactor so long as lower alkylamine and dihaloalkane can be reacted by charging to the reactor.

Preferred reactor are a batch reactor by dropwise addition of dihaloalkane to lower alkaneamine or a batch reactor by dropwise addition of dihaloalkane to lower alkaneamine or a reactor capable of continuous operation, that is, vessel type continuous reactor, more preferably tubular continuous reactor.

These reactors are used in industry for production of some kind of compounds. However, an example of using these reactors for production of N,N'-dialkylalkanediamine with the same object as the invention has not been known.

To such reactor, raw materials of the invention, that is, a prescribed amount of lower alkylamine or lower alkylamine and dihaloalkane is charged, and further a prescribed amount of dihaloalkane is added, continuously or by portions to control the ratio of the residual amount of haloalkaneamine intermediate to lower alkylamine in the reaction system.

When the process of the invention is carried out in a batch reactor equipped with an apparatus for dropwise addition of dihaloalkane, the dihaloalkane is fed into lower alkylamine in order to control the ratio of the residual amount of haloalkaneamine intermediate to lower alkylamine in the reaction system and also to control the ratio of the residual amount of haloalkaneamine intermediate to resultant N,N'-dialkylalkanediamine. Dropwise addition of dihaloalkane is carried out over 1 to 50 hours, preferably over 1.5 to 10 hours.

When a continuous reactor is used, a raw material feeding port is installed in the course of reaction system and the raw material is fed by portions to control the residual amount of haloalkaneamine intermediate in the specified range of the invention.

In the first stage, lower alkylamine can be used in a large excess to dihaloalkane in order to control the amount of haloalkaneamine intermediate within the range which satisfies the scope of the invention. Lower alkylamine is preferably charged in excess to dihaloalkane and dihaloalkane is added from charge ports which are installed at prescribed portions on the continuous reactor, depending upon the residual amount of haloalkaneamine intermediate in the reaction system.

By such methods, the ratio of haloalkaneamine intermediate to lower alkylamine can be controlled and the ratio of haloalkaneamine intermediate to resultant N,N'-dialkylalkanediamine can also be controlled.

The number of stages on the reactor is 1 to 100, preferably 4 to 50.

In the reactor design, required numbers of dihaloalkane feeding ports having the best shape are installed on the best position of each reactor which carries out from initiation to termination of the reaction. The dihaloalkane is fed to each reactor charging lower alkylamine.

The number of dividing dihaloalkane feed to a tubular continuous reactor is 1 to 20, preferably 1 to 10. On designing the tubular reactor, required numbers of dihaloalkane feeding ports having the best shape are installed on the optimum position of the tube between the initiation point and the termination point of the reaction.

When the process of the invention is carried out by using a most favorable tubular continuous reactor, the feeding velocity of lower alkylamine and haloalkane to reactor is 1 cm/sec or more. The reaction time depends upon the reaction temperature, reactor type and raw material feeding velocity, and is preferably 1 minute to 5 hours, more preferably 3 to 30 minutes.

After finishing the reaction, excess lower alkylamine is recovered and the formed product N,N'-dialkylalkanediamine can be isolated by distillation or other separation procedures.

EXAMPLE

The invention will be hereinafter illustrate in detail by way of examples and comparative examples.

Example 1

To a tubular reactor having a thermometer, pressure gauge and diameter of 10 mm, monomethylamine which was previously maintained at 90° C. was continuously fed at a rate of 10.46 kg/hr, and at the same time dichloroethane which was previously maintained at 100° C. was continuously fed at rate of 1.38 kg/hr, The reaction was carried out at 120° C. for 6 minutes. In the course of reaction, the reaction mixture was analyzed by gas chromatography and the amount of N-methyl-2-chloroethylamine intermediate was controlled to 0.0016 mol or less for 1 mol of monomethylamine. After finishing the reaction, excess monomethylamine was recovered and the reaction mass was analyzed by gas chromatography.

As a result, the yield of N,N'-dimethyl-1,2-ethanediamine was 89.0%. By-product N,N'-dimethylpiperazine was 3.0% and by-product N,N',N''-trimethyldiethylenetriamine was 6.5%.

Example 2

To a tubular reactor having a thermometer, pressure gauge and diameter of 10 mm, monomethylamine which was previously maintained at 90° C. was continuously fed at a rate of 10.46 kg/hr, and at the same time dichloroethane which was previously maintained at 100° C. was continuously fed at rate of 0.96 kg/hr, The reaction was carried out at 120° C. for 6 minutes. In the course of reaction, the reaction mixture was analyzed by gas chromatography and the amount of N-methyl-2-chloroethylamine intermediate was controlled to 0.0014 mol or less for 1 mol of monomethylamine. After finishing the reaction, excess monomethylamine was recovered and the reaction mass was analyzed by gas chromatography.

As a result, the yield of N,N'-dimethyl-1,2-ethanediamine was 92.5%. By-product N,N'-dimethylpiperazine was 2.0% and by-product N,N',N''-trimethyldiethylenetriamine was 4.7%.

Example 3

To a tubular reactor having a thermometer, pressure gauge and diameter of 10 mm, monomethylamine which was previously maintained at 90° C. was continuously fed at a rate of 10.46 kg/hr, and at the same time dichloroethane which was previously maintained at 100° C. was continuously fed at a rate of 0.69 kg/hr, The reaction was carried out at 120° C. for 6 minutes. In the course of reaction, the reaction mixture was analyzed by gas chromatography and the amount of N-methyl-2-chloroethylamine intermediate was controlled to 0.001 mol or less for 1 mol of monomethylamine. After finishing the reaction, excess monomethylamine was recovered and the reaction mass was analyzed by gas chromatography.

As a result, the yield of N,N'-dimethyl-1,2-ethanediamine was 93.0%. By-product N,N'-dimethylpiperazine was 2.1% and by-product N,N',N''-trimethyldiethylenetriamine was 4.2%.

Example 4

To a tubular reactor having a thermometer, pressure gauge and diameter of 20 mm, monomethylamine which was previously maintained at 90° C. was continuously fed at a rate of 20.97 kg/hr, and at the same time, dichloroethane which was previously maintained at 100° C. was continuously fed at rate of 2.69 kg/hr, The reaction was carried out at 110° C. for 7 minutes. In the course of reaction, the reaction mixture was analyzed by gas chromatography and the amount of N-methyl-2-chloroethylamine intermediate was controlled to 0.0013 mol or less for 1 mol of monomethylamine. After finishing the reaction, excess monomethylamine was recovered, and the reaction mass was analyzed by gas chromatography.

As a result, the yield of N,N'-dimethyl-1,2-ethanediamine was 87.0%. By-product N,N'-dimethylpiperazine was 4.2% and by-product N,N',N''-trimethyldiethylenetriamine was 6.5%.

Example 5

To a tubular reactor having a thermometer, pressure gauge and diameter of 10 mm, monomethylamine which was previously maintained at 90° C. was continuously fed at a rate of 20.97 kg/hr, and at the same time dichloroethane which was previously maintained at 100° C. was continuously fed at rate of 1.85 kg/hr, The reaction was carried out at 110° C. for 7 minutes. In the course of reaction, the reaction mixture was analyzed by gas chromatography and the amount of N-methyl-2-chloroethylamine intermediate was controlled to 0.00125 mol or less for 1 mol of monomethylamine. After finishing the reaction, excess monomethylamine was recovered, and the reaction mass was analyzed by gas chromatography.

As a result, the yield of N,N'-dimethyl-1,2-ethanediamine was 89.0%. By-product N,N'-dimethylpiperazine was 3.2% and by-product N,N',N''-trimethyldiethylenetriamine was 6.5%.

Example 6

To a tubular reactor having a thermometer, pressure gauge and diameter of 10 mm, monomethylamine which was previously maintained at 90° C. was continuously fed at a rate of 20.97 kg/hr, and at the same time dichloroethane which was previously maintained at 100° C. was continuously fed at rate of 1.38 kg/hr, The reaction was carried out at 110° C. for 7 minutes. In the course of reaction, the reaction mixture was analyzed by gas chromatography and the amount of N-methyl-2-chloroethylamine intermediate was controlled to 0.0011 mol or less for 1 mol of monomethylamine. After finishing the reaction, excess monomethylamine was recovered, and the reaction mass was analyzed by gas chromatography.

As a result, the yield of N,N'-dimethyl-1,2-ethanediamine was 90.2%. By-product N,N'-dimethylpiperazine was 3.2% and by-product N,N',N''-trimethyldiethylenetriamine was 5.5%.

Example 7

To a tubular reactor having a thermometer, pressure gauge and diameter of 10 mm, monomethylamine which was previously maintained at 90° C. was continuously fed at a rate of 20.97 kg/hr. Dichloroethane which was previously maintained at 100° C. was divided into four portions and each portion was simultaneously fed with monoethylamine and continuously fed from four locations on the reactor at a rate of 0.345 kg/hr, respectively, that is, at a total rate of 1.38 kg/hr, The reaction was carried out at 110° C. for 7 minutes. In the course of reaction, the reaction mixture was analyzed by gas chromatography and the amount N-methyl-2-chloroethylamine intermediate was controlled to 0.00105 mol or less for 1 mol of monomethylamine. After finishing the reaction, excess monomethylamine was recovered and the reaction mass was analyzed by gas chromatography.

As a result, the yield of N,N'-dimethyl-1,2-ethanediamine was 91.2%. By-product N,N'-dimethylpiperazine was 2.2% and by-product N,N',N''-trimethyldiethylenetriamine was 5.5%.

Example 8

To a tubular reactor having a thermometer, pressure gauge and diameter of 10 mm, monomethylamine which was previously maintained at 90° C. was continuously fed at a rate of 20.97 kg/hr. Dichloroethane which was previously maintained at 100° C. was divided into eight portions and each portion was simultaneously fed with monomethylamine and continuously fed from eight locations on the reactor at a rate of 0.336 kg/hr, respectively, that is, at a total rate of 2.69 kg/hr, The reaction was carried out at 110° C. for 7 minutes. In the course of reaction, the reaction mixture was analyzed by gas chromatography and the amount of N-methyl-2-chloroethylamine intermediate was controlled to 0.0009 mol for 1 mol of monomethylamine. After finishing the reaction, excess monomethylamine was recovered and the reaction mass was analyzed by gas chromatography.

As a result, the yield of N,N'-dimethyl-1,2-ethanediamine was 92.6%. By-product N,N'-dimethylpiperazine was 2.2% and by-product N,N',N"-trimethyldiethylenetriamine was 4.3%.

Example 9

Vessel type reactor having a thermometer and pressure gauge were connected in series to five stages. Monomethylamine which was previously maintained at 90° C. and dichloroethane which was previously maintained at 90° C. were simultaneously and continuously fed to the reactor individually at a rate of 20.97 kg/hr and 1.86 kg/hr. The mixture was reacted with stirring at 120° C. with a residence time of 20 minutes. In the course of reaction, the reaction mixture was analyzed by gas chromatography and the amount of N-methyl-2-chloroethylamine intermediate was controlled to 0.0011 mol or less for 1 mol of monomethylamine. After finishing the reaction, excess monomethylamine was recovered and the reaction mass was analyzed by gas chromatography.

As a result, the yield of N,N'-dimethyl-1,2-ethanediamine was 90.9%. By-product N,N'-dimethylpiperazine was 2.7% and by-product N,N',N"-trimethyldiethylenetriamine was 5.8%.

Example 10

To a batch reactor equipped with thermometer and pressure gauge, 31.45 kg of monomethylamine was charged and maintained at 120° C. To the reactor, 2.78 kg of dichloroethane was dropwise added over 5 hours. After finishing dropwise addition, excess monomethylamine was recovered and the reaction mass was analyzed by gas chromatography.

As a result, the yield of N,N'-dimethyl-1,2-ethanediamine was 90%. By-product N,N'-dimethylpiperazine was 2.2% and by-product N,N',N"-trimethyldiethylenetriamine was 5.0%.

The amount of N-methyl-2-chloroethylamine intermediate was 0.0006 mol or less for 1 mol of monomethylamine.

Comparative Example 1

Monomethylamine and dichloroethane were previously maintained at 90° C. To a vessel type reactor equipped with a thermometer and pressure gage, monomethylamine was charged at a rate of 20.97 kg/hr and dichloroethane was simultaneously charged at a rate of 1.86 kg/hr.

After finishing charge, the reaction mass was analyzed by gas chromatography. The amount of N-methyl-2-chloroethylamine was 0.0028 mol for 1 mol of monomethylamine. The reaction was carried out with stirring at 120° C. for 2 hours. After finishing the reaction, excess monomethylamine was recovered and the reaction mass was analyzed by gas chromatography. As a result, the yield of N,N'-dimethyl-1,2-ethanediamine was 77.3%. By-product N,N'-dimethylpiperazine was 5.7% and by-product N,N',N"-trimethyldiethylenetriamine was 15.8%.

POSSIBILITY FOR UTILIZATION IN INDUSTRY

The reaction of dihaloalkane with lower alkylamine by the invention can inhibit formation of by-products cyclic dialkylalkanediamine and trialkylalkanetriamine and can provide N,N'-dialkylalkanediamine in high yield within a short time.

Thus, the present invention is an excellent preparation process in industry.

What is claimed is:

1. A preparation process of N,N'-dialkylalkanediamine by reacting dihaloalkane represented by the formula (1):

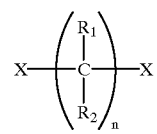

(1)

wherein $R_1$ and $R_2$ are a hydrogen atom or a lower alkyl group, X is a chlorine, bromine or iodine atom, and n is an integer of 2 to 6, with lower alkylamine represented by the formula (2):

$$R-NH_2 \tag{2}$$

wherein R is a lower alkyl group, to obtain N,N'-dialkylalkanediamine represented by the formula (3):

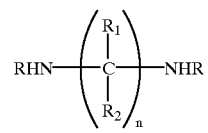

(3)

wherein $R_1$ and $R_2$ are a hydrogen atom or a lower alkyl group, X is a chlorine, bromine or iodine atom, and n is an integer of 2 to 6, characterized in that the reaction is carried out with controlling the residual amount of haloalkaneamine intermediate represented by the formula (4):

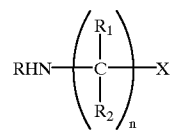

(4)

wherein R is a lower alkyl group, $R_1$ and $R_2$ are a hydrogen atom or a lower alkyl group, X is a chlorine, bromine or iodine atom, and n is an integer of 2 to 6, to 0.002 mol or less for 1 mol of lower alkylamine represented by the formula (2).

2. A preparation process according to claim 1 wherein the lower alkylamine represented by the formula (2) is used in amount of 5 mols or more for 1 mol of dihaloalkane represented by the formula (1).

3. A preparation process according to claim 1 wherein the reaction of dihaloalkane with lower alkylamine is carried out by dropwise addition of dihaloalkane to lower alkylamine in a batch reactor.

4. A preparation process according to claim 1 wherein the reaction of dihaloalkane with lower alkylamine is carried out in a vessel type continuous reactor or a tubular continuous reactor.

5. A preparation process according to claim 1 wherein the reaction of dihaloalkane with lower alkylamine is carried out in a multistage vessel type continuous reactor.

6. A preparation process according to claim 1 wherein the reaction of dihaloalkane with lower alkylamine is carried out in a tubular continuous reactor.

7. A preparation process according to claim 6 wherein the reaction is carried out by feeding dihaloalkane represented by the formula (1) and lower alkylamine represented by the formula (2) to a tubular continuous reactor, and dihaloalkane is added by portions or continuously at a position capable of controlling a residual amount in the reactor tube of haloalkaneamine represented by the formula (4), to 0.002 mol or less for 1 mol of lower alkylamine.

8. A preparation process according to claim 7, wherein the residual amount in the reaction system of haloalkaneamine represented by the formula (4) is 0.001 mol or less for 1 mol of lower alkylamine represented by formula (2).

9. A preparation process according to claim 8, wherein the reaction is carried out at temperature of 50 to 250° C.

10. A preparation process according to claim 6, wherein the residual amount in the reaction system of haloalkaneamine represented by the formula (4) is 0.001 mol or less for 1 mol of lower alkylamine represented by formula (2).

11. A preparation process according to claim 5, wherein the residual amount in the reaction system of haloalkaneamine represented by the formula (4) is 0.001 mol or less for 1 mol of lower alkylamine represented by formula (2).

12. A preparation process according to claim 4, wherein the residual amount in the reaction system of haloalkaneamine represented by the formula (4) is 0.001 mol or less for 1 mol of lower alkylamine represented by formula (2).

13. A preparation process according to claim 3, wherein the residual amount in the reaction system of haloalkaneamine represented by the formula (4) is 0.001 mol or less for 1 mol of lower alkylamine represented by formula (2).

14. A preparation process according to claim 2, wherein the residual amount in the reaction system of haloalkaneamine represented by the formula (4) is 0.001 mol or less for 1 mol of lower alkylamine represented by formula (2).

15. A preparation process according to claim 1, wherein the residual amount in the reaction system of haloalkaneamine represented by the formula (4) is 0.001 mol or less for 1 mol of lower alkylamine represented by formula (2).

16. A preparation process according to claim 7, wherein the reaction is carried out at temperature of 50 to 250° C.

17. A preparation process according to claim 6, wherein the reaction is carried out at temperature of 50 to 250° C.

18. A preparation process according to claim 5, wherein the reaction is carried out at temperature of 50 to 250° C.

19. A preparation process according to claim 4, wherein the reaction is carried out at temperature of 50 to 250° C.

20. A preparation process according to claim 3, wherein the reaction is carried out at temperature of 50 to 250° C.

21. A preparation process according to claim 2, wherein the reaction is carried out at temperature of 50 to 250° C.

22. A preparation process according to claim 1, wherein the reaction is carried out at temperature of 50 to 250° C.

* * * * *

UNITED STATES PATENT AND TRADEMARK OFFICE
CERTIFICATE OF CORRECTION

| | |
|---|---|
| PATENT NO. | : 6,242,651 B1 |
| DATED | : June 5, 2001 |
| INVENTOR(S) | : Yasuhiro Takano et al. |

It is certified that error appears in the above-identified patent and that said Letters Patent is hereby corrected as shown below:

<u>Column 12,</u>
Line 42, delete "X is a chlorine, bromine or iodine atom" and replace with -- R is a lower alkyl group --.

Signed and Sealed this

Seventh Day of May, 2002

Attest:

JAMES E. ROGAN
*Director of the United States Patent and Trademark Office*

*Attesting Officer*